United States Patent
Liddicoat et al.

(10) Patent No.: US 6,942,694 B2
(45) Date of Patent: Sep. 13, 2005

(54) TISSUE ANNULOPLASTY BAND AND APPARATUS AND METHOD FOR FASHIONING, SIZING AND IMPLANTING THE SAME

(75) Inventors: John R. Liddicoat, Sewickley, PA (US); Brian Colyer Coppom, Longmont, CO (US); Richard B. Streeter, Winchester, MA (US)

(73) Assignee: Viacor, Inc., Danvers, MA (US)

( * ) Notice: Subject to any disclaimer, the term of this patent is extended or adjusted under 35 U.S.C. 154(b) by 0 days.

(21) Appl. No.: 09/760,222

(22) Filed: Jan. 12, 2001

(65) Prior Publication Data

US 2001/0049558 A1 Dec. 6, 2001

Related U.S. Application Data

(60) Provisional application No. 60/176,046, filed on Jan. 14, 2000.

(51) Int. Cl.$^7$ .................................................. A61F 2/24
(52) U.S. Cl. ....................................................... 623/2.36
(58) Field of Search .............................. 623/2.36, 2.41, 623/2.38, 2.4

(56) References Cited

U.S. PATENT DOCUMENTS

| | | | |
|---|---|---|---|
| 5,669,919 A | 9/1997 | Sanders et al. | |
| 5,709,695 A * | 1/1998 | Northrup, III | 606/148 |
| 5,769,780 A | 6/1998 | Hata et al. | |
| 5,891,159 A * | 4/1999 | Sherman et al. | 606/144 |
| 6,001,127 A | 12/1999 | Schoon et al. | |
| 6,102,945 A | 8/2000 | Campbell | |
| 6,174,332 B1 * | 1/2001 | Loch et al. | 623/2.37 |
| 6,368,348 B1 * | 4/2002 | Gabbay | 623/2.36 |

FOREIGN PATENT DOCUMENTS

| WO | WO 93/02640 A1 | 2/1993 |
|---|---|---|

\* cited by examiner

*Primary Examiner*—Corrine McDermott
*Assistant Examiner*—William H Matthews
(74) *Attorney, Agent, or Firm*—Pandiscio & Pandiscio, P.C.

(57) ABSTRACT

This invention relates to a system used to fashion, size, and implant a tissue annuloplasty band. This system comprises (1) a device to cut tissue; (2) a device to fashion (i.e., roll, fold, bunch, etc.) the tissue into a band (i.e., the tissue annuloplasty band); and (3) a sizer that comprises an mounting ring which allows for determining and maintaining the proper size and shape of the tissue annuloplasty band while it is attached to the annulus of a heart valve. These components can be used alone, together as a system, or in any combination to fashion, size, and/or implant the tissue annuloplasty band.

13 Claims, 16 Drawing Sheets

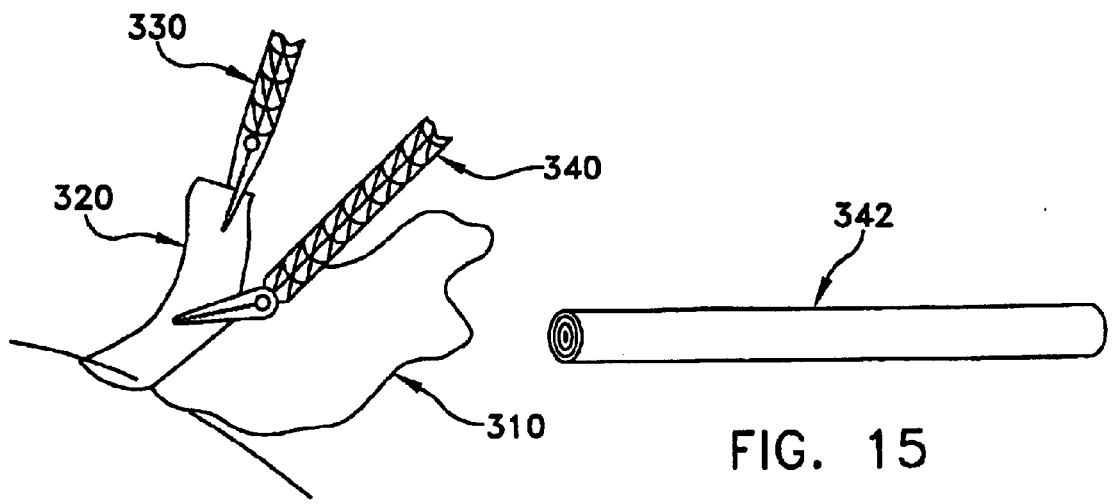
FIG. 14
FIG. 15
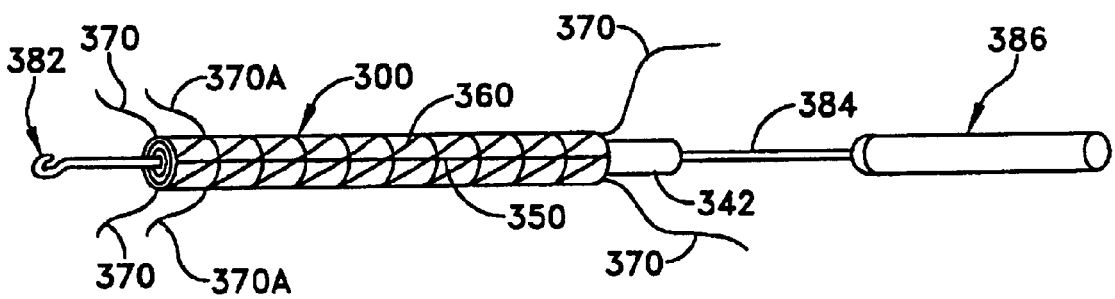
FIG. 16
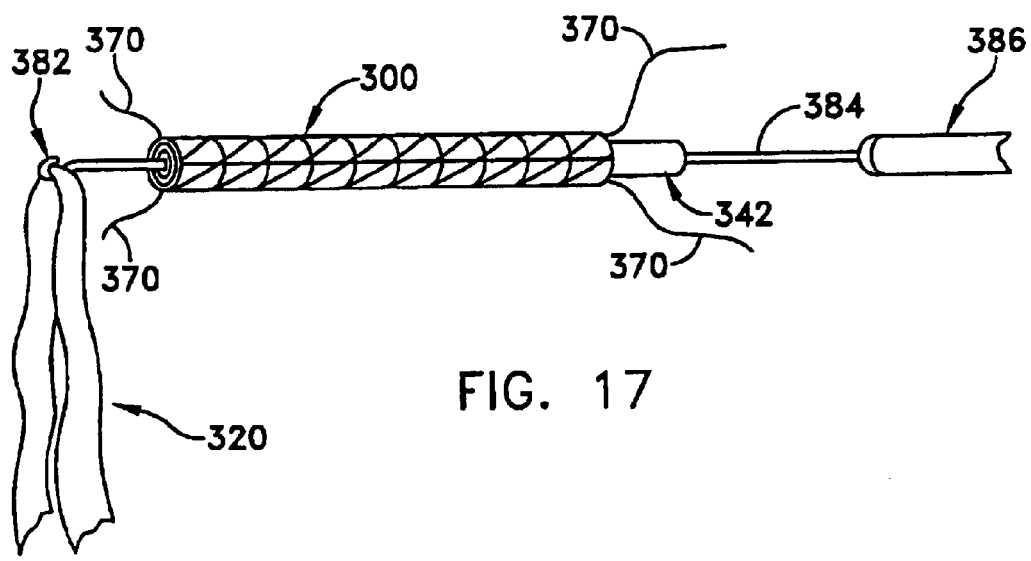
FIG. 17

TISSUE ANNULOPLASTY BAND AND APPARATUS AND METHOD FOR FASHIONING, SIZING AND IMPLANTING THE SAME

REFERENCE TO PENDING PRIOR PATENT APPLICATION

This patent application claims benefit of pending prior U.S. Provisional Patent Application Ser. No. 60/176,046, filed Jan. 14, 2000 by John R. Liddicoat et al. for INSTRUMENTS AND METHODS TO FASHION, SIZE, AND IMPLANT A TISSUE ANNULOPLASTY DEVICE, which patent application is hereby incorporated herein by reference.

FIELD OF THE INVENTION

The present invention relates to the correction of valvular heart disease. In particular, it relates to the fashioning, sizing and implanting of tissue as an annuloplasty band or ring to be used for the correction of valvular heart disease.

BACKGROUND OF THE INVENTION

The human heart comprises four heart valves. Two of these valves are located between the left and right atria and ventricles and are called the mitral and tricuspid valves, respectively. These valves serve to maintain one-way blood flow into the ventricles and to prevent the regurgitation of blood back into the atria. Although the present invention can be used for many different applications including mitral and tricuspid valve repair, for the purposes of example it will hereinafter be described in connection with the repair of a mitral valve.

Mitral valve repair is the surgical procedure of choice to correct mitral regurgitation of all etiologies. With the use of current surgical techniques, approximately 70 to 95% of all regurgitant mitral valves can be repaired. The advantages of mitral valve repair over mitral valve replacement are well documented. These advantages include better preservation of cardiac function and reduced risk of anticoagulant-related hemorrhage, thromboembolism and endocarditis.

Nearly all mitral valve repairs include an annuloplasty. The annuloplasty consists of implanting a prosthetic band or ring that surrounds all or part of the circumference of the annulus of the valve. The annuloplasty serves several functions: it remodels the annulus, decreases tension on suture lines, increases leaflet coaptation, and prevents recurrent annular dilation. In addition, the annuloplasty improves repair durability.

The placement of a prosthetic annuloplasty band or ring in the heart results in a risk of thromboembolism and infection; these risks are unavoidable and persist for the life of the patient. Formation of blood clots on prosthetic materials in the heart often results in stroke, and infection of a prosthetic annuloplasty band or ring may lead to life-threatening sepsis and the need for urgent re-operation.

The ideal annuloplasty would be effected using a universally flexible, autologous material. Such a material does in fact exist, in the form of the patient's own pericardium. The pericardium is the sac in which the heart sits. The pericardium is often used by heart surgeons to repair congenital heart defects. It heals well, and almost never becomes infected. However, the pericardium can be difficult to work with.

In order to make practical use of autologous pericardium for a mitral valve annuloplasty, the surgeon would need apparatus to facilitate the creation of a tissue annuloplasty band or ring of the appropriate length and thickness, and to ensure that the tissue annuloplasty band or ring will maintain the chosen dimensions while it is applied to the heart.

The development of a system for constructing and deploying a pericardial annuloplasty band or ring would have great benefit for the patient. No prosthetic material would be placed in the heart, greatly reducing the risk of thromboembolism and infection. No anticoagulation would be necessary. In addition, pericardium remains flexible as it heals, and this would result in preserved mitral valve physiology.

SUMMARY OF THE INVENTION

It is, therefore, an object of the present invention to provide a pericardial annuloplasty band.

Another object of the present invention is to provide apparatus and methods that facilitate the construction of a precisely measured annuloplasty band from the patient's own pericardium.

Still another object of the present invention is to provide a template upon which the fashioned tissue annuloplasty band is mounted, facilitating sizing and placement of the tissue annuloplasty band in the heart and ensuring that the tissue annuloplasty band maintains its shape during application.

These and other objects are addressed by the present invention which comprises a tissue annuloplasty band and apparatus and methods for fashioning, sizing and implanting the same. In one preferred form of the present invention, the graft tissue is first cut to an appropriate size. Then the cut tissue is fashioned into the appropriate shape, i.e., an elongated length. If desired, an internal or external support structure may be provided to help support and/or manipulate the elongated length of tissue. Next, the elongated length of tissue is mounted onto an adjustable mounting ring so as to form a tissue annuloplasty band. Then the appropriate size and shape of the tissue annuloplasty band is determined. This is done by directly measuring the mitral valve, or by placing the tissue annuloplasty band (which is mounted on the adjustable mounting ring) in the left atrium and visually comparing it against the patient's mitral valve. The size of the tissue annuloplasty band is then adjusted, by adjusting the size of the adjustable mounting ring, until the tissue annuloplasty band is the appropriate size. Any excess tissue is marked for later excision. Next, sutures are placed through the patient's annulus and through the tissue annuloplasty band, which is still seated on the adjustable mounting ring. The tissue annuloplasty band is then guided into place with the assistance of the adjustable mounting ring. Then the tissue annuloplasty band is tied down into place, while the tissue annuloplasty band is still mounted onto the adjustable mounting ring, so as to maintain its shape and length during final seating. Once the tissue annuloplasty band has been tied into place, the tissue annuloplasty band is dismounted from the adjustable mounting ring. The adjustable mounting ring is then removed, and any excess tissue previously marked is excised.

In another preferred form of the invention, the adjustable mounting ring may be replaced by a set of pre-sized mounting rings. In this case, an appropriate one of the pre-sized mounting rings is selected by directly measuring the mitral valve or by placing different pre-sized mounting rings in the left atrium and visually comparing them against the patient's mitral valve. Once the appropriate pre-sized mounting ring has been selected, the elongated length of graft tissue is mounted onto the pre-sized mounting ring and then the remainder of the annuloplasty is performed in the manner described above.

BRIEF DESCRIPTION OF THE DRAWINGS

These and other objects and features of the present invention will be further disclosed in the following detailed description of the preferred embodiments of the invention, which is to be considered together with the accompanying drawings wherein like numbers refer to like parts and further wherein:

FIG. 14 is a schematic view showing manual sizing of the graft tissue used for the tissue annuloplasty band;

FIG. 15 is a schematic view of a guide tube used to help guide the graft tissue through an external mesh;

FIG. 16 is a schematic view showing the external mesh, guide tube and tissue hook;

FIG. 17 is a schematic view showing the graft tissue prior to being drawn into the guide tube;

DETAILED DESCRIPTION OF THE PREFERRED EMBODIMENTS

This invention relates to the rapid fashioning, sizing, and implanting of a tissue annuloplasty band for the general purpose of cardiac valve repair. Although the description provided herein describes the use of the system for mitral valve repair, the apparatus and method may be used for other applications as well. Therefore, the following description is intended merely as an example of how the apparatus and method of the present invention may be used, and not by way of limitation.

In accordance with the present invention, the graft tissue (i.e., pericardium, vein, or other autologous or non-autologous tissue) is first cut to an appropriate size. This may be done with any appropriate cutting tool. Preferably, however, a male/female cutting die is used to cut the tissue into the general size and shape appropriate to create the tissue annuloplasty band.

Figure 1:
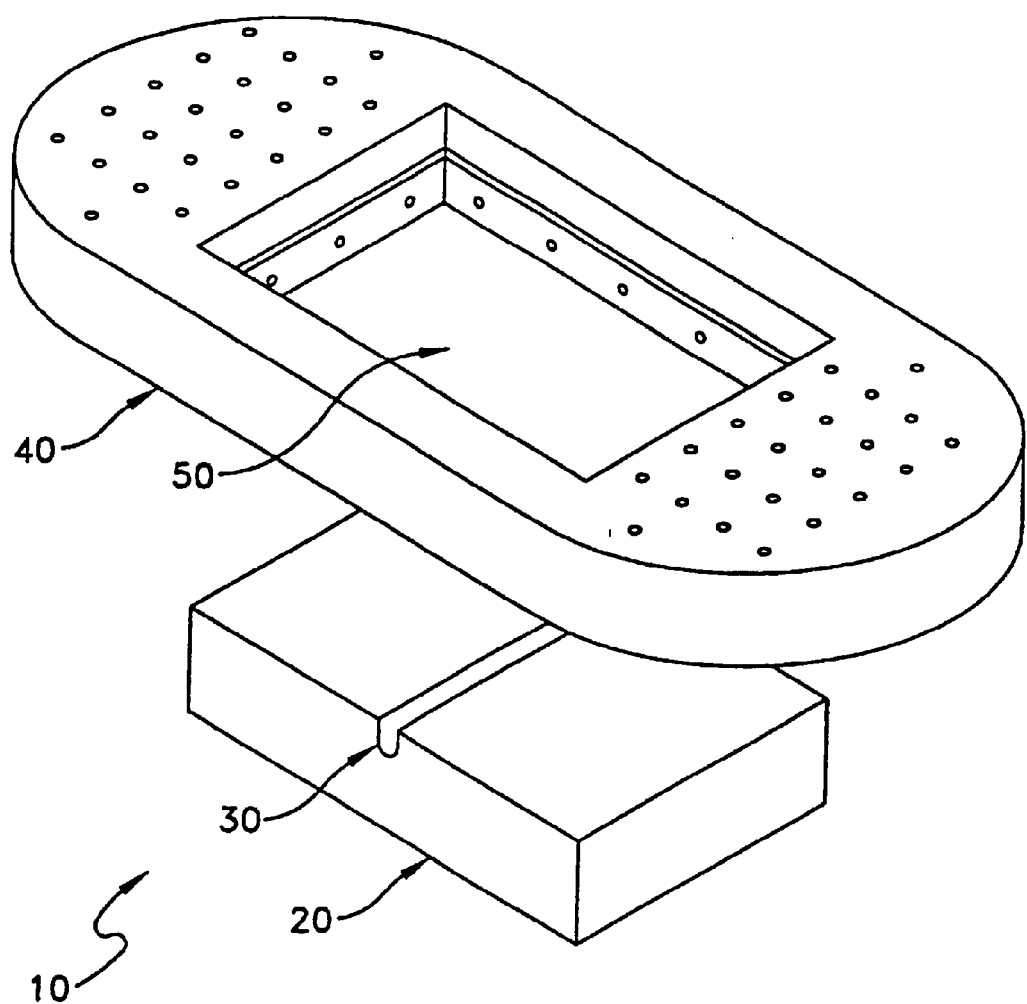
FIG. 1 is a schematic view of a male/female cutting die used in one preferred form of the invention.

More particularly, and looking now at FIG. 1, there is shown a male/female cutting die 10. Cutting die 10 comprises a male die 20 having a groove 30 formed therein, and a female die 40 having a window 50 formed therein. When a piece of donor tissue (e.g., pericardium) is placed between male die 20 and female die 40, and the two die members are thereafter brought together, a piece of graft tissue (corresponding in size to window 50 in female die 40) will be cut from the donor tissue.

Once the graft tissue has been cut to an appropriate size, it is then fashioned into the appropriate shape, i.e., an elongated length. This may be done by rolling, folding, bunching, etc.

Figure 2:
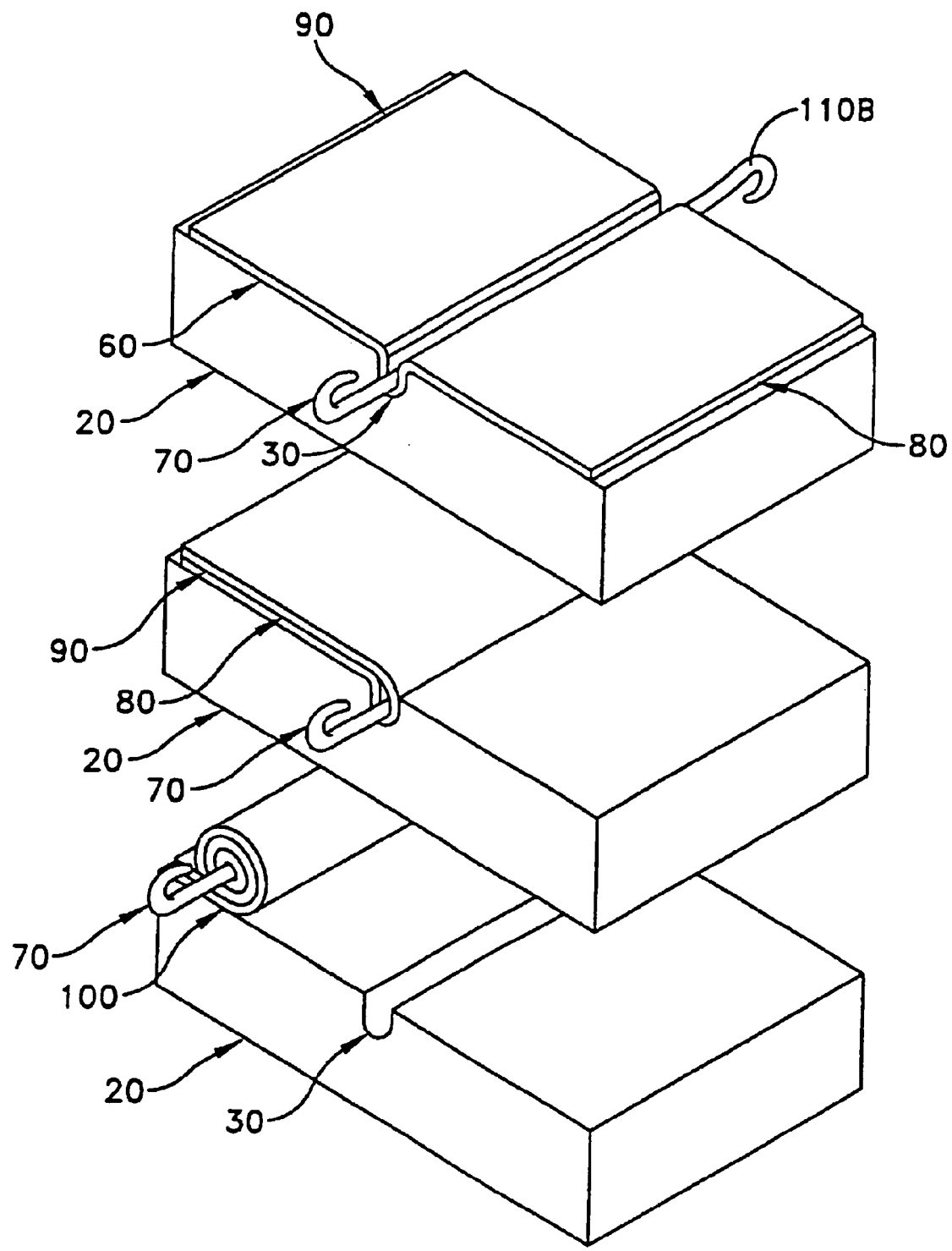
FIG. 2 is a schematic view showing graft tissue being rolled into the tissue annuloplasty band while on the male cutting die.
Figure 3:
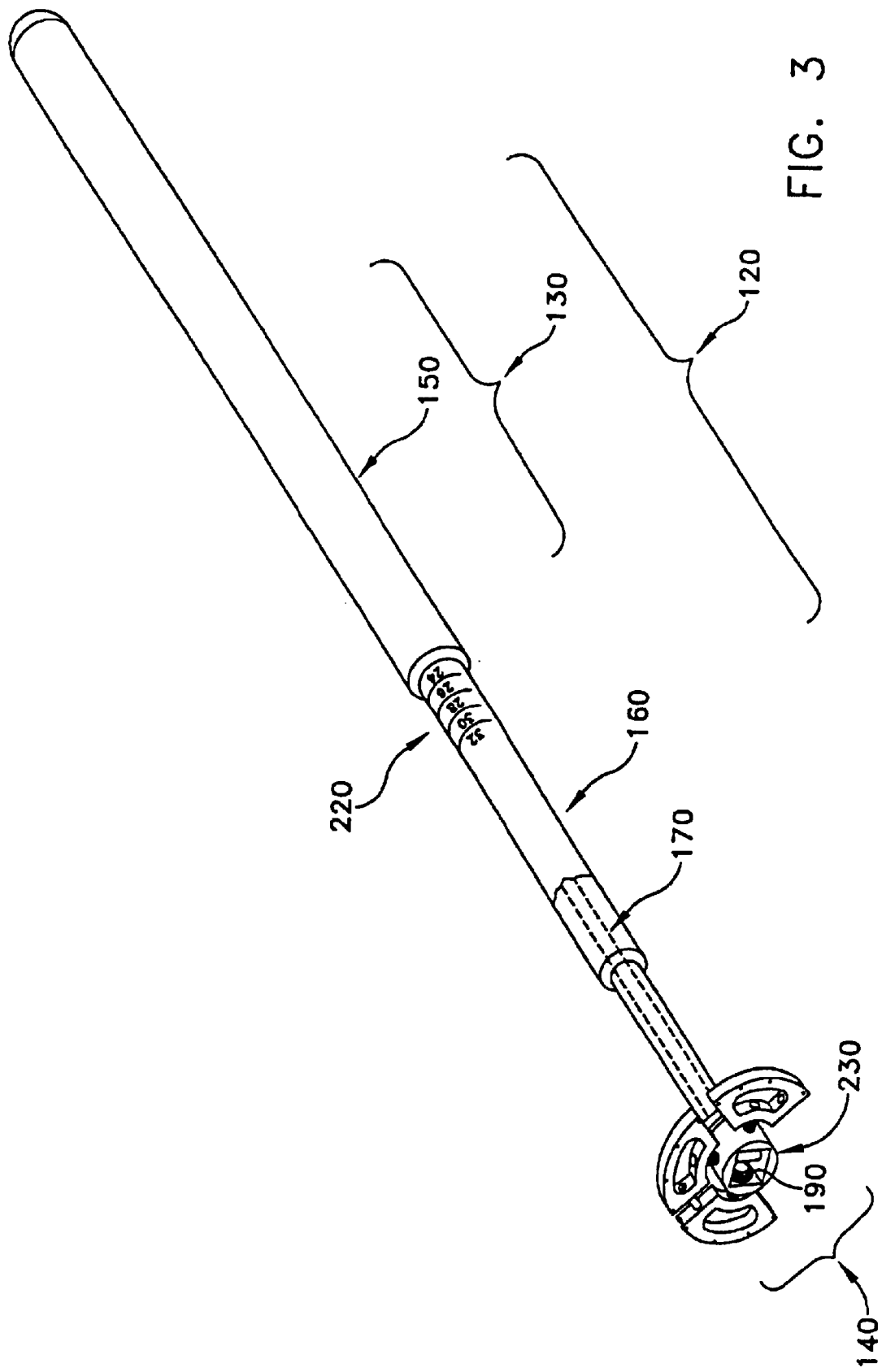
FIG. 3 is a schematic view showing a first sizer formed in accordance with the present invention, with the first sizer's handle extending perpendicular to the plane of the sizer's adjustable mounting ring.
Figure 4:
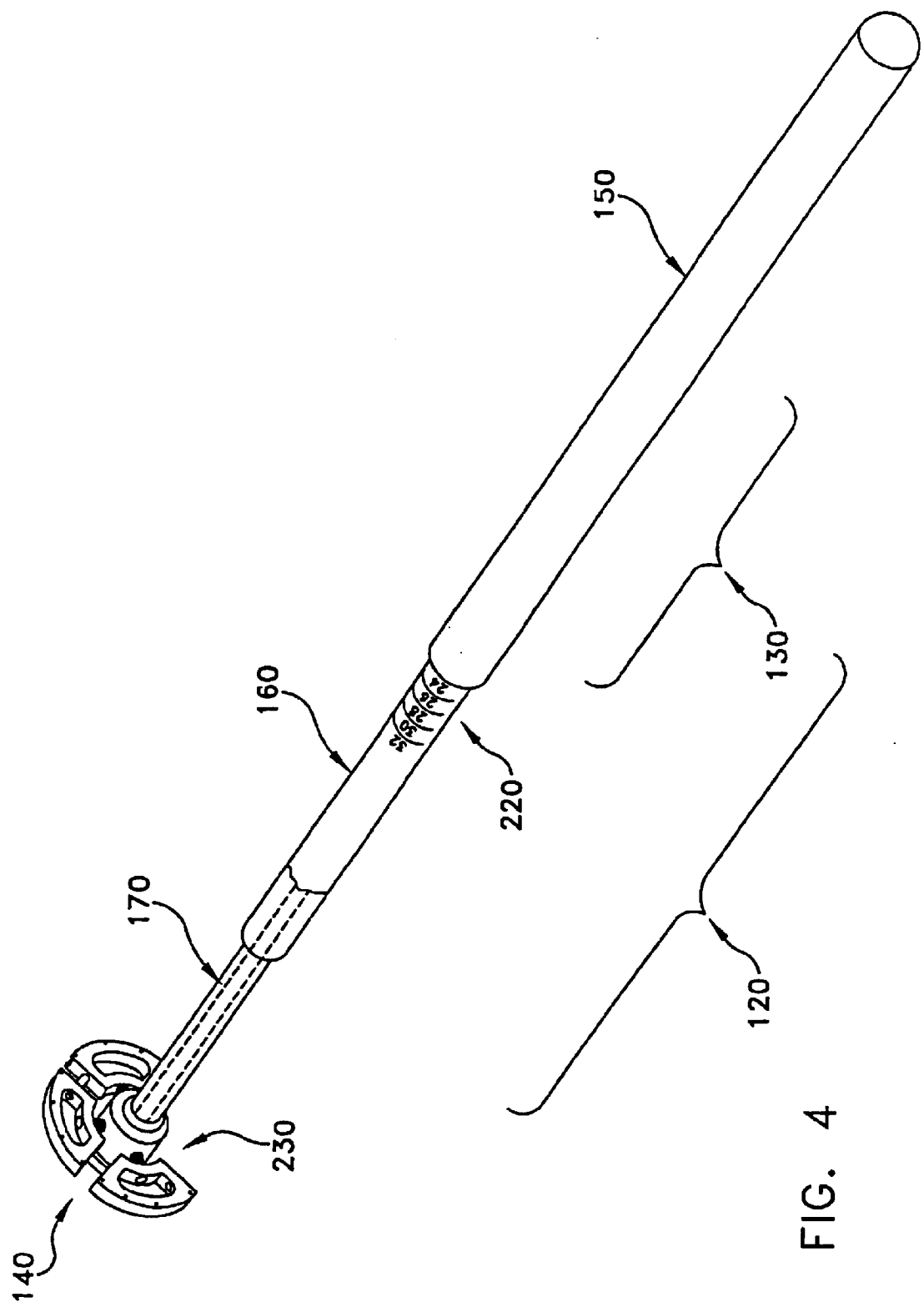
FIG. 4 is a view like that of FIG. 3, except showing the rear side of the first sizer shown in FIG. 3.
Figure 5:
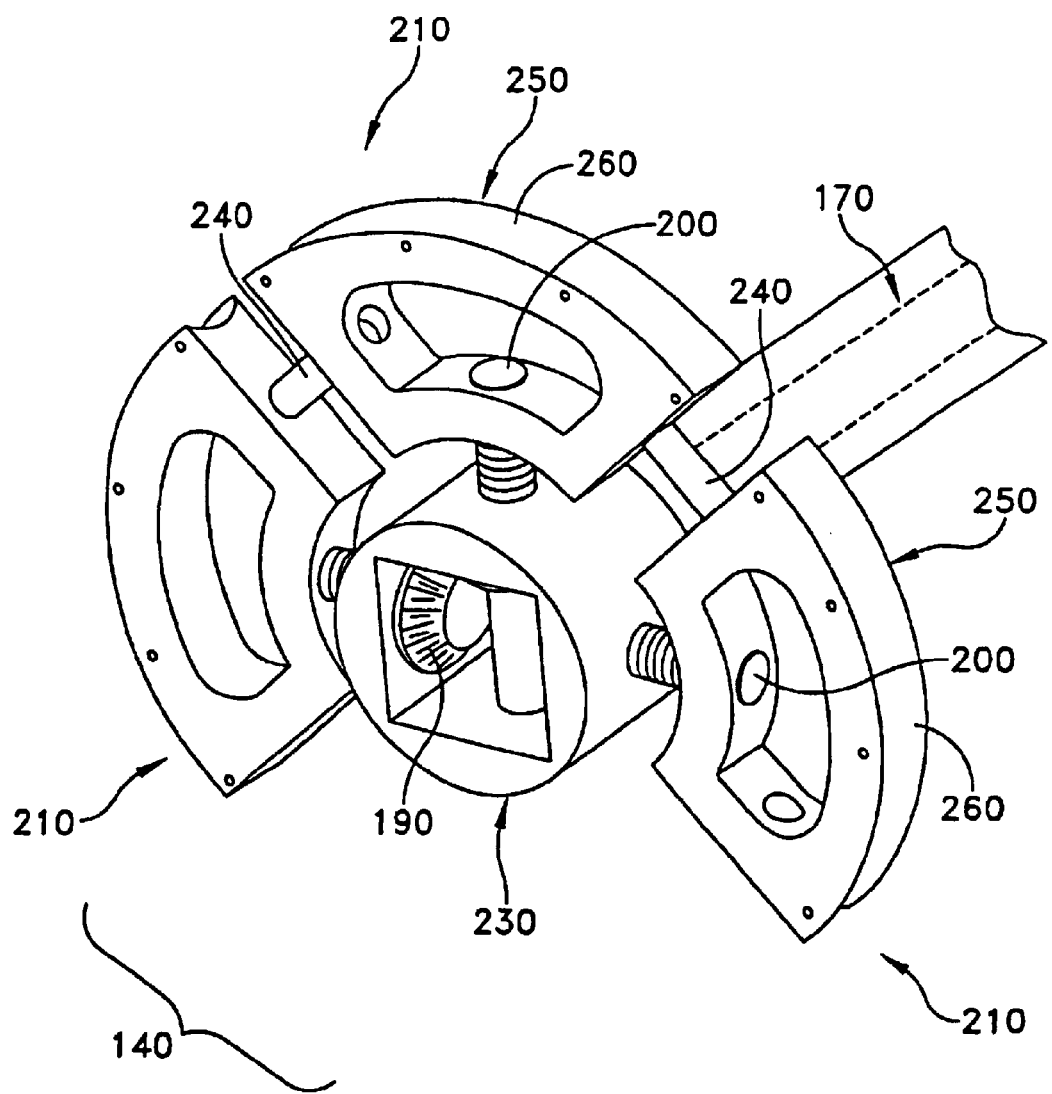
FIG. 5 is a schematic view of the distal end of the first sizer, with the adjustable mounting ring being shown in its largest diameter configuration.
Figure 6:
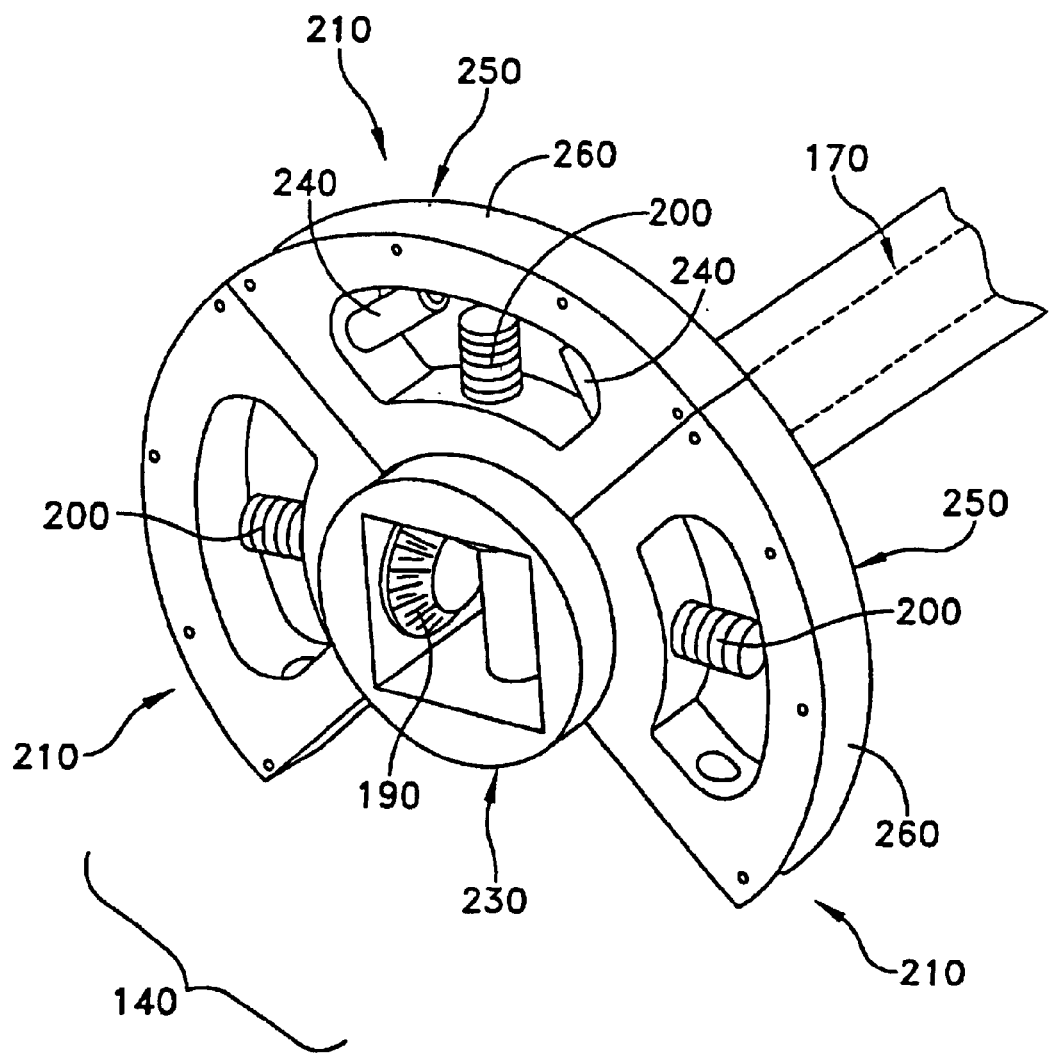
FIG. 6 is a schematic view of the distal end of the first sizer, with the adjustable mounting ring being shown in its smallest diameter configuration.
Figure 7:
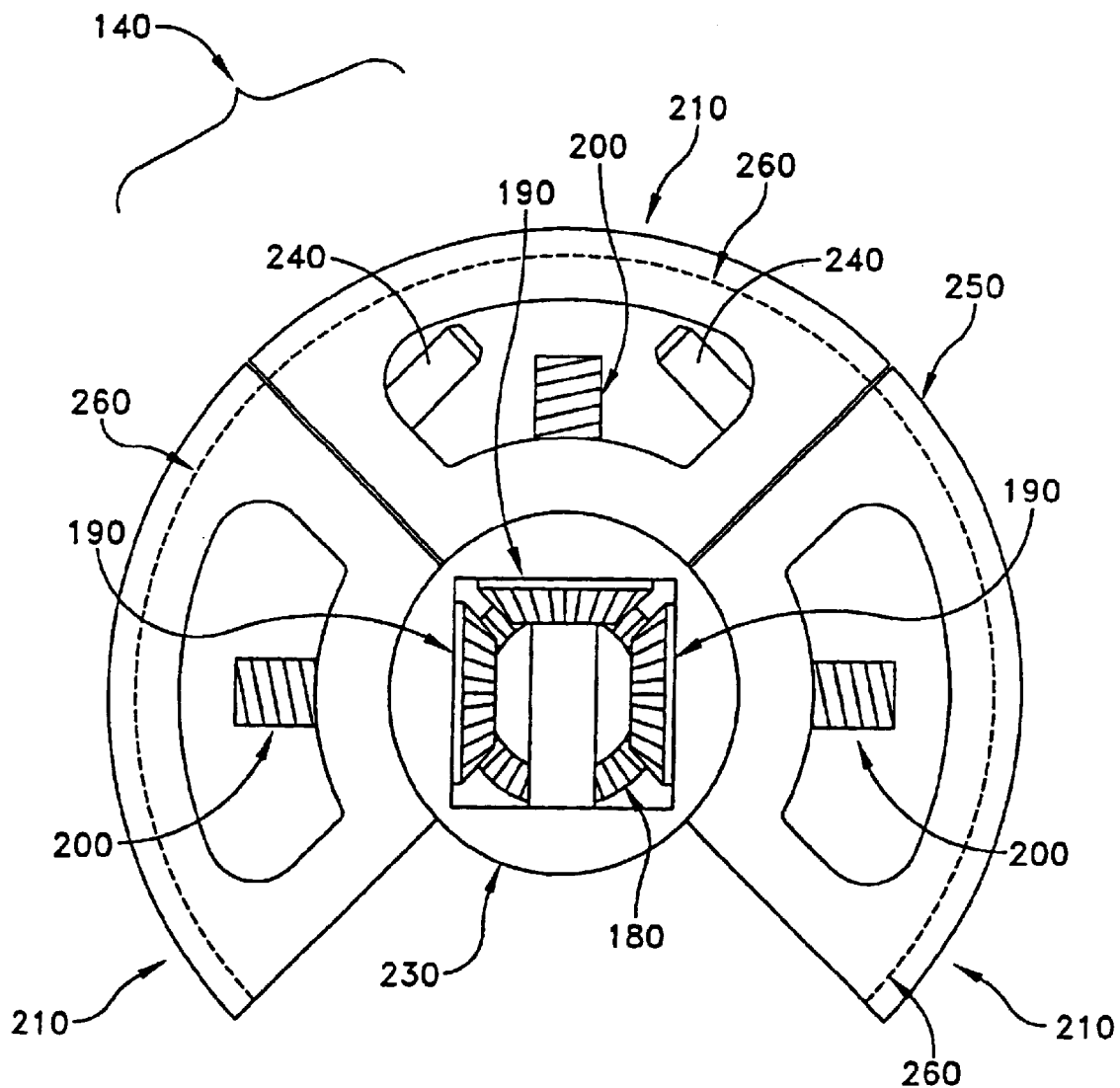
FIG. 7 is a schematic end view of the distal end of the first sizer, with the adjustable mounting ring being shown in its smallest diameter configuration.
Figure 8:
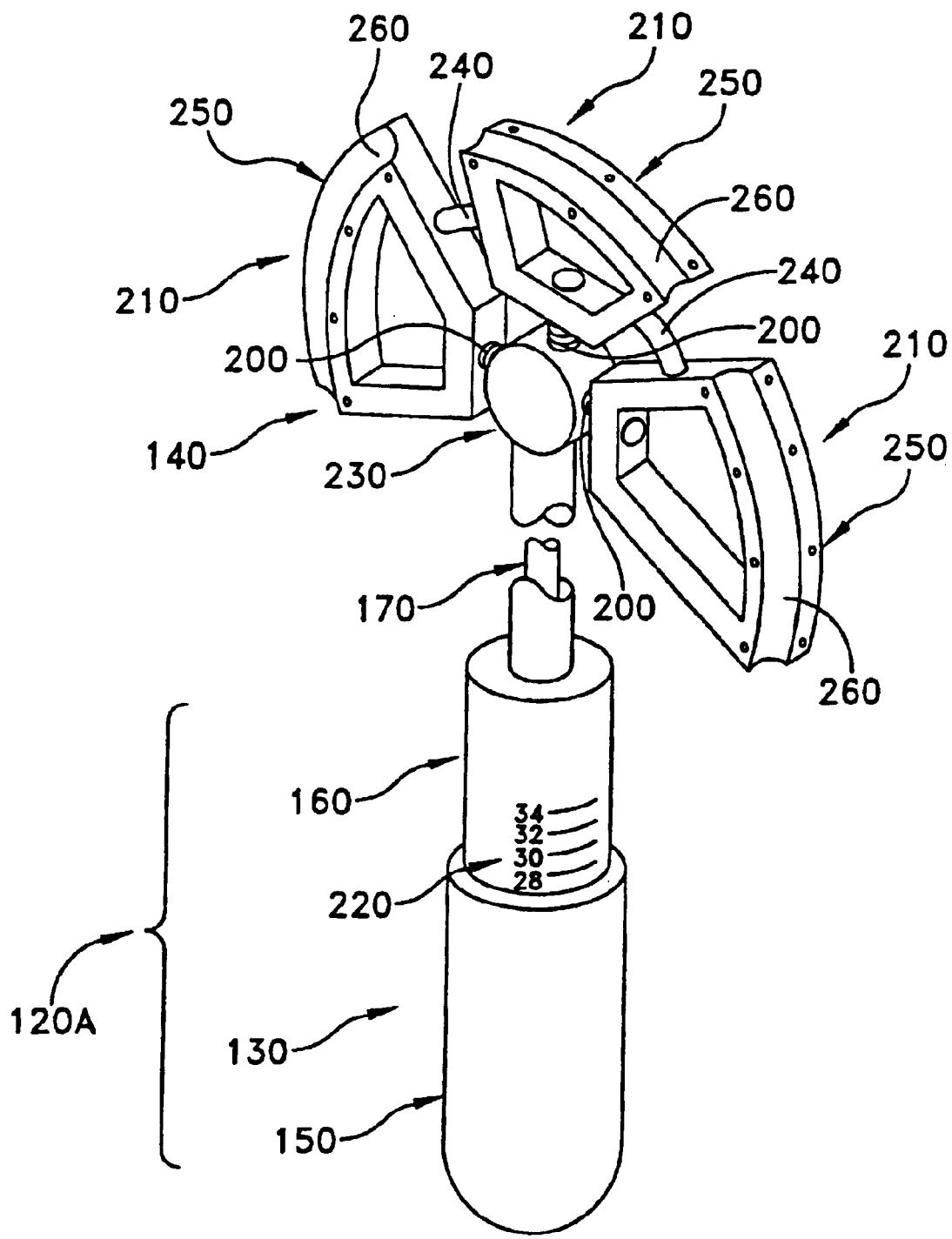
FIG. 8 is a schematic view showing a second sizer formed in accordance with the present invention, with the second sizer's handle extending parallel to the plane of the sizer's adjustable mounting ring.
Figure 9:
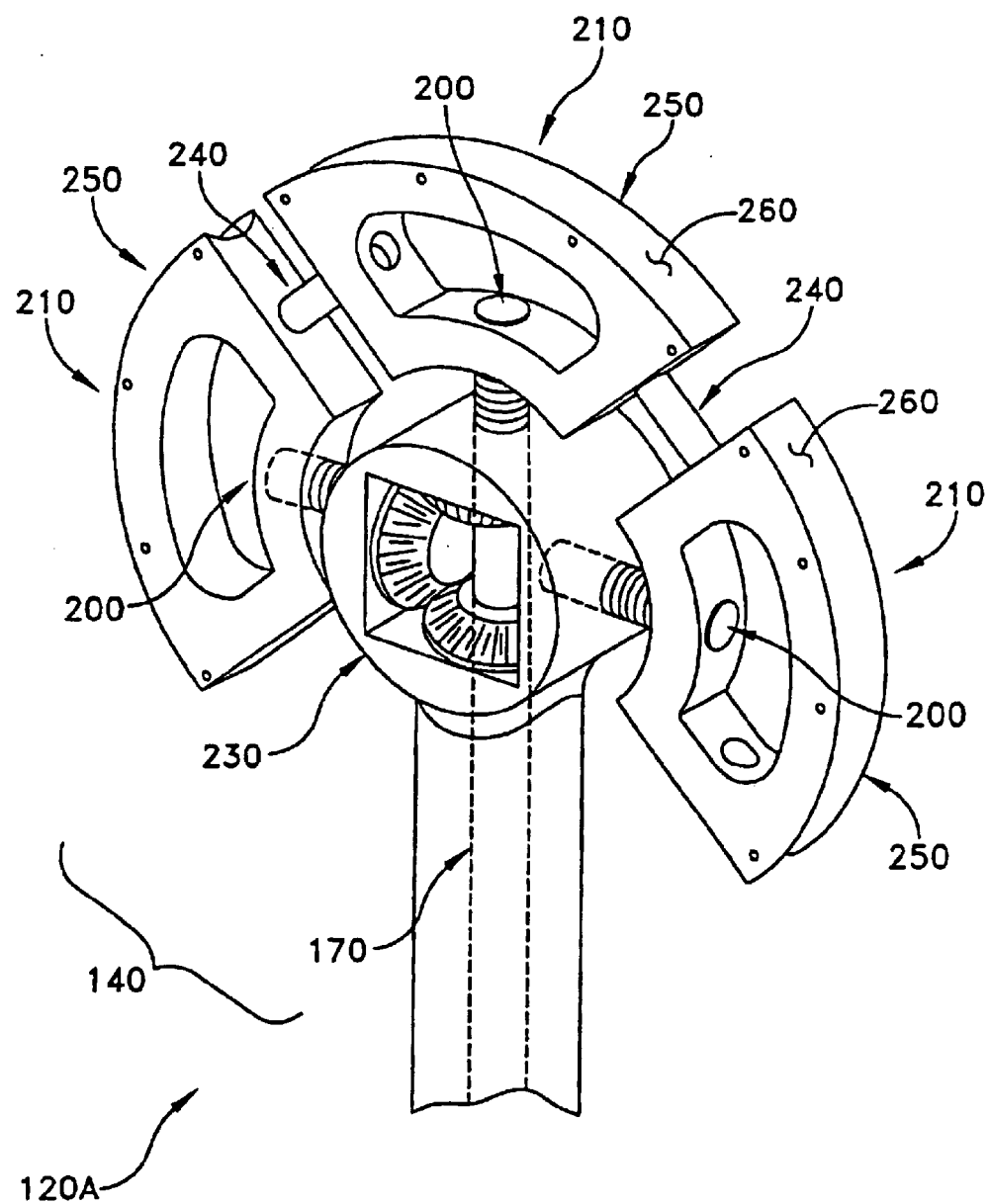
FIG. 9 is a schematic view of the distal end of the second sizer, with the adjustable mounting ring being shown in its largest diameter configuration.
Figure 10:
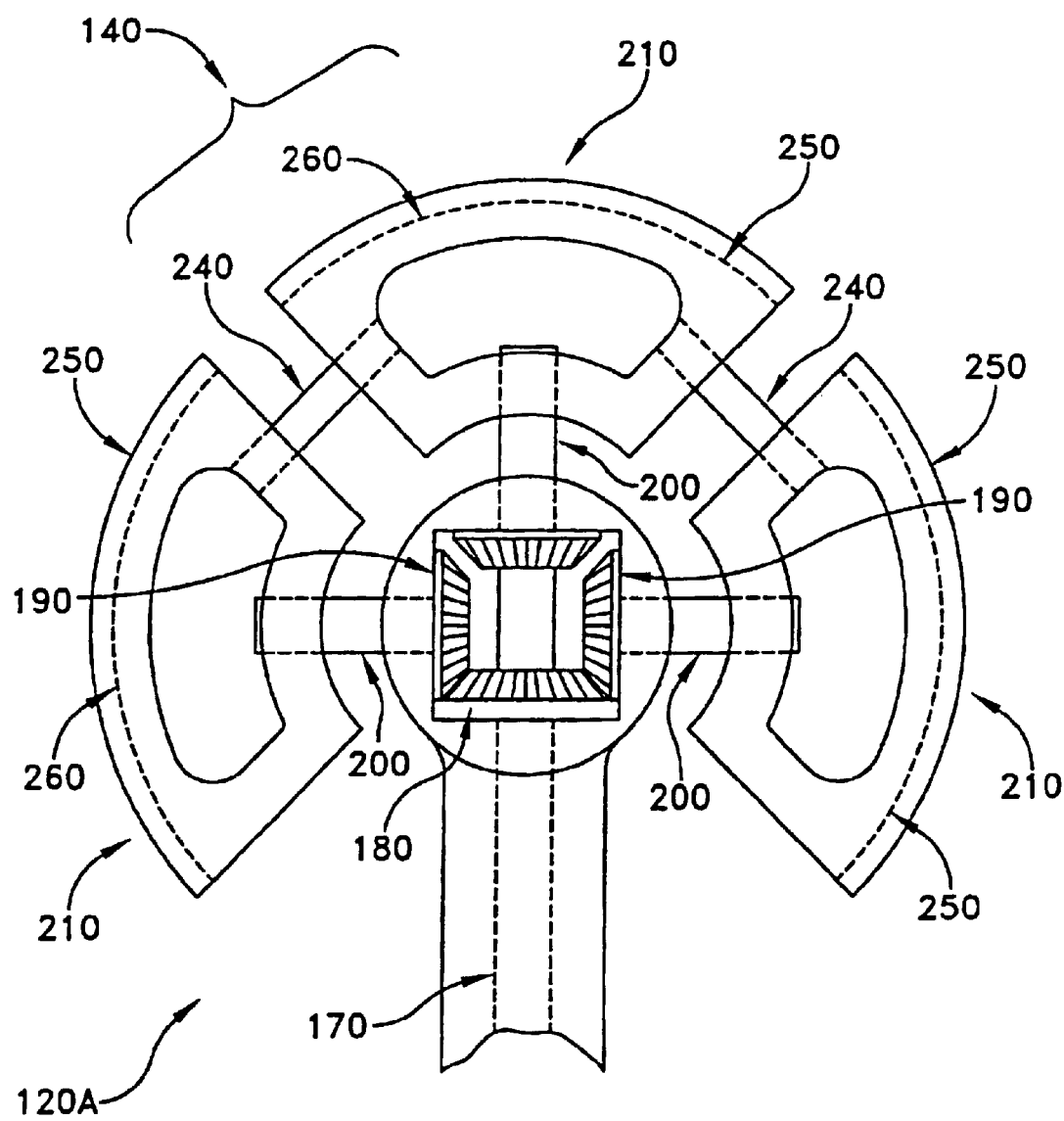
FIG. 10 is a schematic side view of the distal end of the second sizer, with the adjustable mounting ring being shown in its largest diameter configuration.
Figure 11:
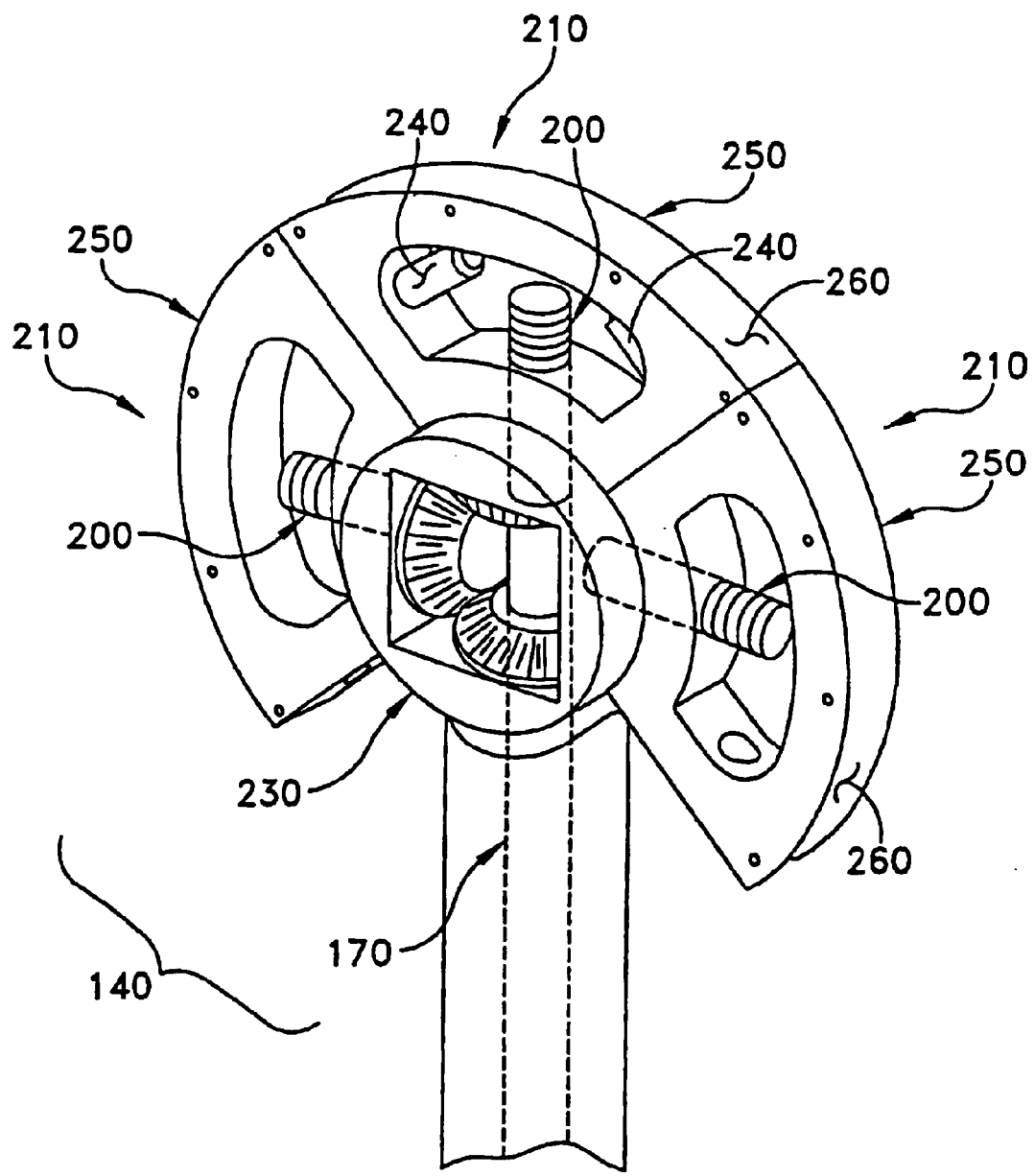
FIG. 11 is a schematic view of the distal end of the second sizer, with the adjustable mounting ring being shown in its smallest diameter configuration.

In one preferred form of the invention, the tissue is rolled about an axle using the male die as the base. More particularly, and looking now at FIG. 2, after a piece of graft tissue 60 has been cut, and while graft tissue 60 is lying on male die 20, an axle 70 is pressed down into groove 30. Then one tissue end 80 is folded over the other tissue end 90, and axle 70 is rolled, so as to form a tissue annuloplasty band 100. If desired, an adhesive, a sealant, a medication or the like may be applied to the tissue. By way of example, an adhesive might be applied to a final rolled edge so as to keep the tissue annuloplasty band from unrolling. Axle 70 is made of a relatively flexible material such as pliable plastic or metal. The body of the axle, while being flexible, may or may not stretch along its linear axis. The two ends 110A, 110B of axle 70 preferably have elastic properties, allowing these portions of the axle to stretch along their linear axis.

Once the graft tissue has been rolled into tissue annuloplasty band 100, it is mounted onto a mounting ring for sizing and implanting. This may be implemented in a variety of ways, using a variety of devices.

In one preferred form of the invention, and looking now at FIGS. 3–7, a first sizer 120 is used. First sizer 120 comprises a handle 130 and an adjustable mounting ring 140. Handle 130 preferably comprises two cylinders 150, 160 which are able to move relative to one another. Cylinder 150 is connected to mounting ring 140 by a drive cable 170 (shown in phantom). Drive cable 170 is in turn connected to a central bevel gear 180 (FIG. 7) in adjustable mounting ring 140. Rotation of central bevel gear 180 in turn causes the additional bevel gears 190 to rotate. These bevel gears 190 are coupled to threaded shafts 200. Adjustable mounting ring segments 210 are internally threaded and ride on the threaded shafts 200. The rotation of threaded shafts 200 causes mounting ring segments 210 to move radially and hence causes adjustable mounting ring 140 to expand and contract (i.e., to change in radial dimension). Accordingly, it will be seen that rotation of cylinder 150 relative to cylinder 160 results in a change in the geometry (i.e., the size) of adjustable mounting ring 140. Cylinder 160 (i.e., the one that is not connected to adjustable mounting ring 140 by drive cable 170) serves as the support portion of the handle and remains in a relatively fixed orientation with respect to adjustable mounting ring 140. Cylinder 160 may have a constant outer diameter or, alternatively, it may have a stepped outer diameter such as that shown in FIGS. 3 and 4. Handle 130 also has a size indicator 220 on the outside of cylinder 160 that shows the size of the tissue annuloplasty band after it has been properly sized.

As mentioned above, adjustable mounting ring 140 is (i) connected to cylinder 150 by drive cable 170, and (ii) fixed to cylinder 160. Adjustable mounting ring 140 comprises a central body 230 that contains the aforementioned bevel gears 180 and 190. These gears 180 and 190 are in turn coupled to the mounting ring segments 210 to which the tissue annuloplasty band 100 will be attached. These mounting ring segments 210 are attached to central body 230 by the threaded shafts 200. Accordingly, movement of the aforementioned bevel gear 180 via cable 170 causes the mounting ring segments 210 to expand and contract relative to central body 230. Hence, the tissue annuloplasty band 100 can be adjusted to the appropriate size for varying patient anatomies. Mounting ring segments 210 can have additional support, e.g., by lateral stays 240 interacting with each other. The outer edge 250 of each segment 210 preferably has a groove 260 in which the tissue annuloplasty band 100 is mounted.

With the aforementioned first sizer 120, the sizer's handle 130 extends perpendicular to the plane of the sizer's adjustable mounting ring 140. Alternatively, and looking now at FIGS. 8–11, there is shown a second sizer 120A in which the sizer's handle 130 extends parallel to the plane of the sizer's adjustable mounting ring 140.

Figure 12:
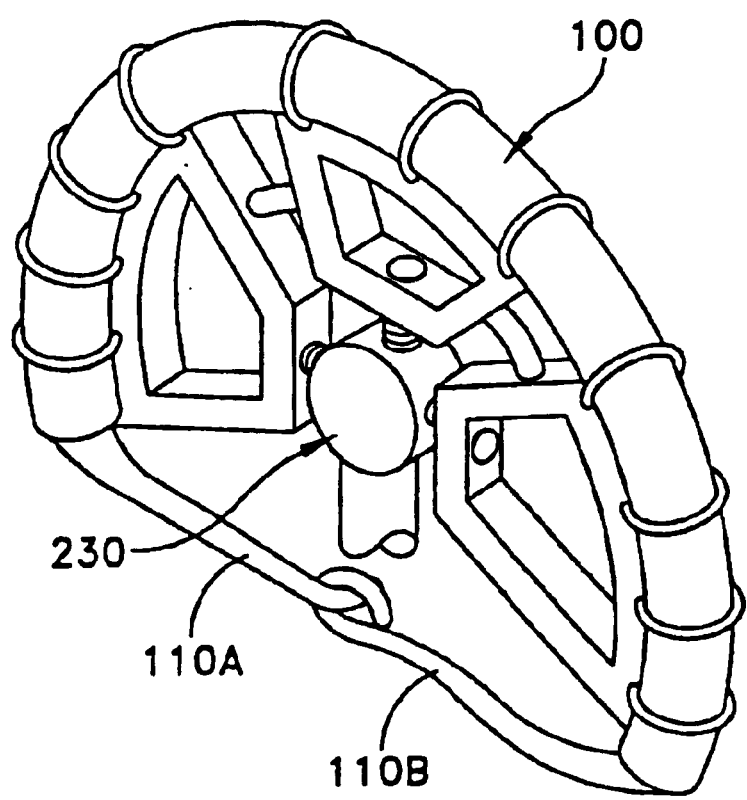
FIG. 12 is a schematic view showing the tissue annuloplasty ring mounted on the second sizer's adjustable mounting ring.

The tissue annuloplasty band 100 (FIG. 2) is placed into groove 260 on adjustable mounting ring 140 (FIG. 12). Then the elastic ends 110A, 110B of axle 70 are attached to one another. This creates tension on the tissue, which keeps the tissue annuloplasty band 100 in the groove 260 on the mounting ring. Clamps, ties or sutures can be applied as necessary for increased stability.

Next, the appropriate size and shape of the tissue annuloplasty band 100 is determined. To do this, the tissue annuloplasty band 100, which is now mounted on adjustable mounting ring 140, is placed in the patient's left atrium and visually compared to the patient's mitral valve. Alternatively, the mitral valve may be measured directly. The surgeon then adjusts the size of tissue annuloplasty band 100 by turning cylinder 150 of handle 130 until tissue annuloplasty band 100 is appropriately sized. Any excess tissue is marked for later excision.

Next, sutures are placed through the patient's annulus and subsequently through the tissue annuloplasty band 100. The tissue annuloplasty band 100 is then guided into place with the assistance of sizer 120 (or 120A). Tissue annuloplasty band 100 is then tied down into place, while it is still mounted on adjustable mounting ring 140, so as to maintain its shape during final seating. Once tissue annuloplasty band 100 has been tied into place, the elastic ends 110A, 110B of axle 70 are detached from one another. Any other stabilizing components such as clamps, ties, or sutures that aided in mounting tissue annuloplasty band 100 to adjustable mounting ring 140 are detached. Adjustable mounting ring 140 is then removed, and axle 70 is withdrawn. Any excess tissue previously marked is excised.

If desired, sizer 120 (120A) can be constructed so that handle 130 may be detached from adjustable mounting ring 140. With such a construction, handle 130 may be removed after guiding tissue annuloplasty band 100 to the surgical site, but before the band is removed from adjustable mounting ring 140.

Figure 13:
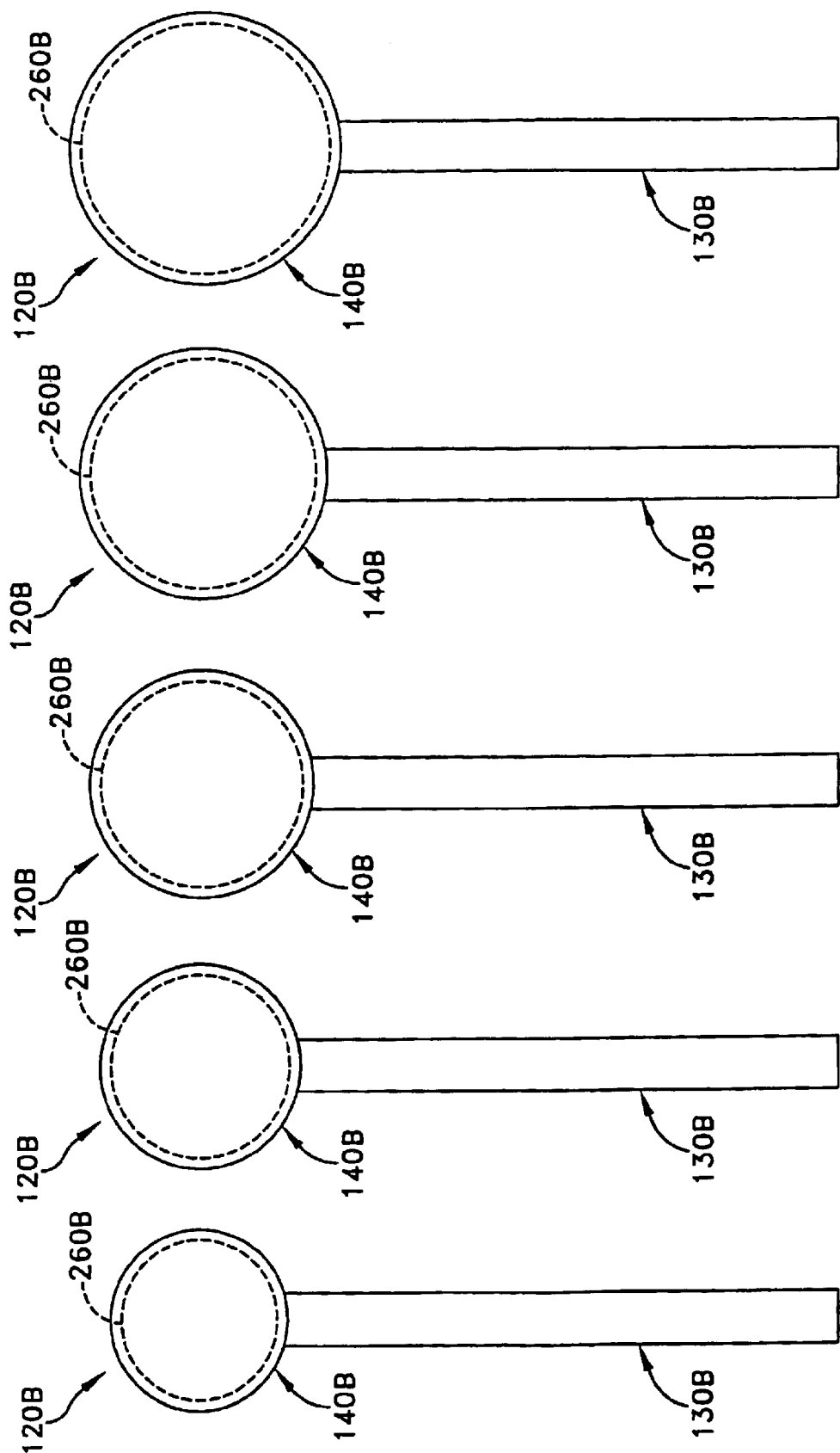
FIG. 13 is a schematic view showing a set of third sizers, wherein each of the third sizers comprises a pre-sized mounting ring.
Figure 22:
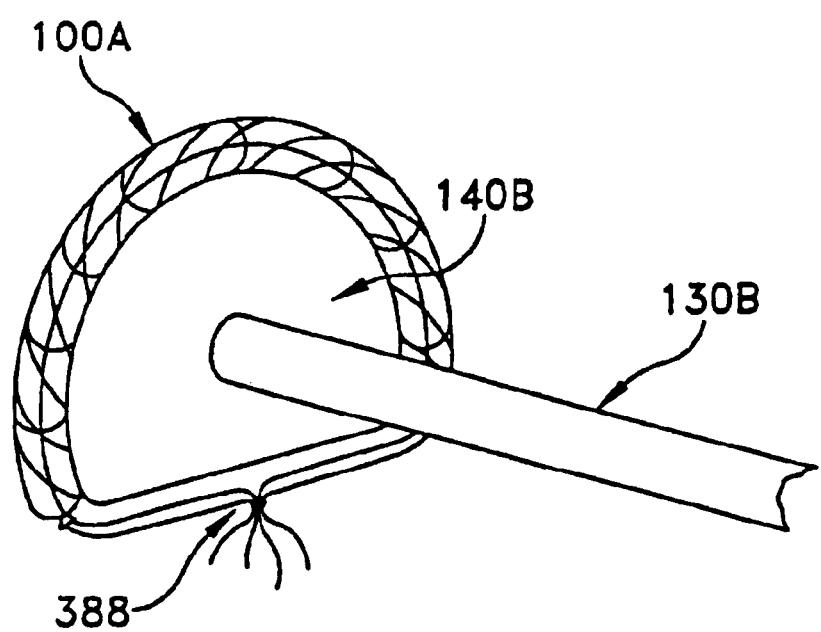
FIG. 22 is a schematic view showing the tissue annuloplasty band attached to a pre-sized, fixed-diameter mounting ring.

It is also possible to practice the present invention using a pre-sized, fixed diameter mounting ring. More particularly, and looking now at FIG. 13, there is shown a set of third sizers 120B, wherein each of the third sizers 120B comprises a pre-sized, fixed diameter mounting ring 140B (preferably having a peripheral groove 260B) and an associated handle 130B. Each mounting ring 140B may comprise a complete circle (e.g., as shown in FIG. 13) or only a portion of a circle (e.g., as shown in FIG. 22). In this form of the invention, an appropriate one of the pre-sized mounting rings 140B is selected by directly measuring the mitral valve or by placing different pre-sized mounting rings in the left atrium and visually comparing them against the patient's mitral valve. Once the appropriate pre-sized mounting ring 140B has been selected, tissue annuloplasty band 100 (FIG. 2) is mounted onto the pre-sized mounting ring 140B, i.e., by slipping tissue annuloplasty band 100 into the peripheral groove 260B and attaching elastic ends 110A, 110B of axle 70 together. Then tissue annuloplasty band 100 is transferred to the annulus of the patient's mitral valve in the manner previously described.

In another preferred form of the invention, and looking at FIGS. 14–22, a tissue annuloplasty band 100A (FIG. 20) is formed using an external structural mesh 300 (FIG. 16). More particularly, graft tissue 310 (FIG. 14) is cut into a preferred long length 320 using a tissue grasper 330 and a tissue cutter 340, both being standard, commercially-available devices. To aid in inserting tissue length 320 into external mesh 300, a temporary guide tube 342 (FIG. 15) may be used to hold open the external mesh 300 and guide the tissue length 320 through the mesh.

Looking at FIG. 16, external mesh 300 is preferably constructed of flexible but not stretchable material such as monofilament or braided suture for permanent implantation into the body. The weave is preferably constructed such that mesh 300 does not stretch in the direction of the long axis via straight members 350. The weave could also provide a large mesh 360 to allow a significant amount of tissue to be exposed to the implant surface so as to promote implant-to-body tissue in-growth. Purse string sutures 370 at the end of mesh 300 provide a means to secure the tissue graft 320 inside the external mesh and to secure the resulting tissue annuloplasty band 100A to the mounting ring 140 (or 140B). If various lengths of bands are required, either individual bands could be provided or a longer band could be cut to the required length. If a longer band is cut to length, extra sets of purse string sutures 370A provide a means to shorten the band and still secure the tissue 320 within the external mesh. Any unused purse string sutures 370, 370A can be cut prior to fixation of the band to the mounting ring.

Looking at FIG. 16, guide tube 342 has been inserted through external mesh 300 to provide a smooth path for tissue 320. A tissue hook 382 and shaft 384 are inserted through guide tube 342, and then tissue 320 is folded in half and inserted through hook 382 (FIG. 17). For this embodiment, tissue 320 must be at least twice as long as the pre-sized band length. An alternative to hook 382 is a grasper (not shown) that pulls a single length of tissue through guide tube 342. For such an alternative embodiment, a single length of tissue might be wider than a folded length of tissue, such that the volume of tissue inside the external mesh 300 is similar in both embodiments.

Figure 18:
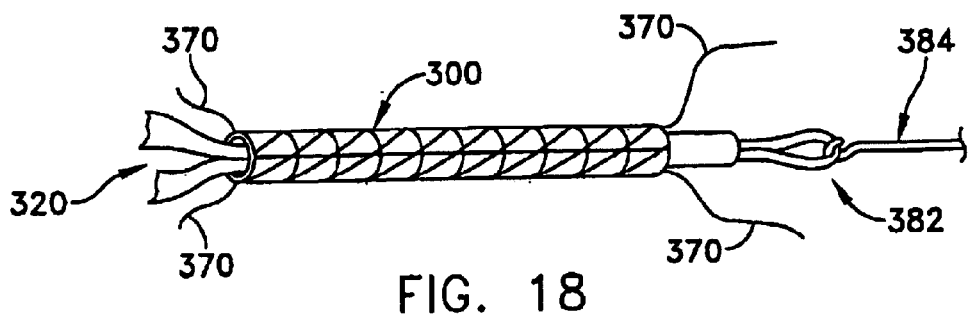
FIG. 18 is a schematic view showing the graft tissue after it has been drawn into the guide tube.
Figure 19:
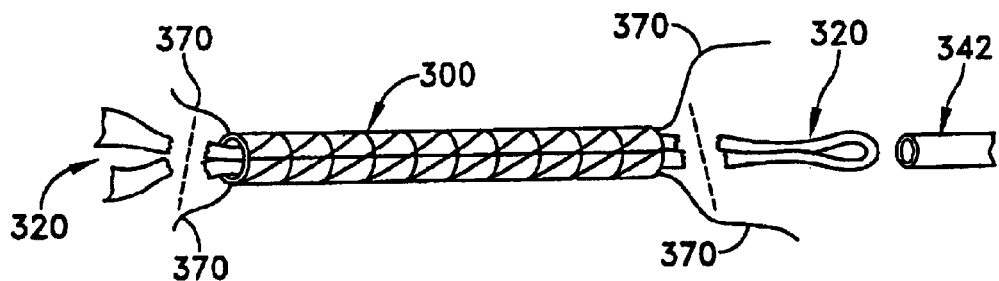
FIG. 19 is a schematic view showing the guide tube being removed and the tissue being cut to fit the external mesh.
Figure 20:
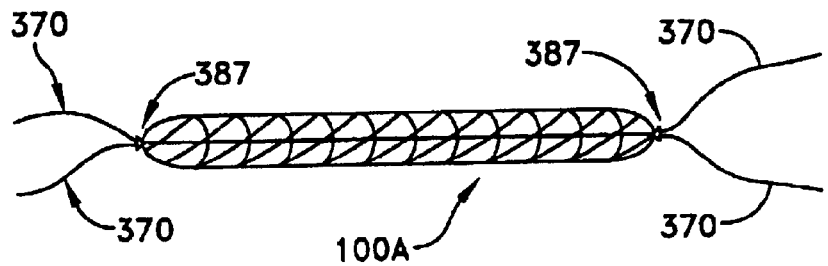
FIG. 20 is a schematic view showing the tissue secured within the external mesh and after synching the end pursestring sutures closed, forming the tissue annuloplasty band.

Looking next at FIGS. 18–20, the tissue 320 is pulled through guide tube 400 by pulling on tissue retraction handle 386. Guide tube 342 is then pulled out from between tissue 320 and external mesh 300. Any excess tissue 320 is cut to the length of external mesh 300 and purse string sutures 370 are tied closed at 387 to secure the tissue 320 within external mesh 300, forming a properly sized tissue annuloplasty band 100A.

Figure 21:
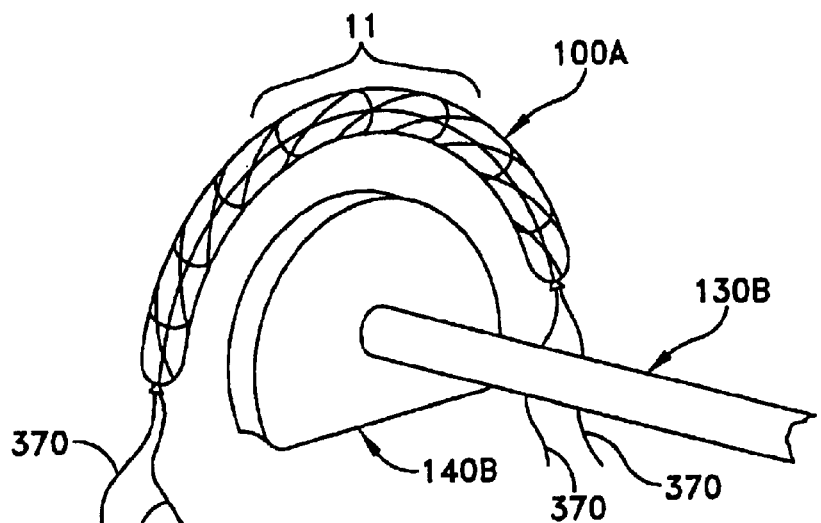
FIG. 21 is a schematic view showing the tissue annuloplasty band being attached to a pre-sized (i.e., fixed-diameter) mounting ring.

Looking at FIGS. 21 and 22, tissue annuloplasty band 100A is temporarily secured to a mounting ring (e.g., a pre-sized fixed-diameter mounting ring 140B) by tying a knot 388 (FIG. 22) using the remaining lengths of purse string sutures 370. Once the surgeon has sutured the tissue annuloplasty band 100A to the mitral valve using standard surgical techniques, mounting ring 140B is removed by cutting and retrieving purse string sutures 370 close to the ends of tissue annuloplasty band 100A.

It is to be understood that the present invention is by no means limited to the particular constructions and method steps disclosed above and/or shown in the drawings, but also comprises any modifications or equivalents within the scope of the claims.

What is claimed is:

1. An annuloplasty band comprising an elongated substantially solid body of overlaid layers of graft tissue, said body being of a selected length and configured to be flexed into a generally curved configuration, and the band being configured to be sutured to a valvular annulus, said band being substantially solid throughout the length thereof, and said overlaid layers being formed by spirally wound graft tissue.

2. An annuloplasty band according to claim 1 wherein said graft tissue comprises pericardium.

3. An annuloplasty band according to claim 1 wherein said graft tissue comprises autologous tissue.

4. An annuloplasty band according to claim 1 further comprising a support structure attached to said graft tissue.

5. An annuloplasty band according to claim 4 wherein said support structure is internal to said graft tissue.

6. An annuloplasty band according to claim 5 wherein said support structure comprises a centrally disposed axial structure.

7. An annuloplasty band according to claim 6 wherein said axial structure comprises an intermediate section terminating in a pair of opposing ends, and further wherein said intermediate section is flexible.

8. An annuloplasty band according to claim 7 wherein said opposing ends are elastic.

9. An annuloplasty band according to claim 7 wherein said opposing ends are adapted to connect to one another.

10. An annuloplasty band according to claim 7 wherein said axial structure is formed out of plastic.

11. An annuloplasty band according to claim 7 wherein said axial structure is formed out of metal.

12. An annuloplasty band according to claim 1 wherein at least one of an adhesive, a sealant and a medication is applied to the graft tissue.

13. An annuloplasty band according to claim 1, wherein said overlaid layers of graft tissue comprise a sheet of graft tissue rolled upon itself and tightly packed to form a generally cylindrical shape.

* * * * *